(12) United States Patent
Bradley (10) Patent No.: US 9,511,222 B2
(45) Date of Patent: Dec. 6, 2016

(54) SYSTEM AND METHOD FOR POST-STROKE NEURAL REHABILITATION

(71) Applicant: BOSTON SCIENTIFIC NEUROMODULATION CORPORATION, Valencia, CA (US)

(72) Inventor: Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 419 days.

(21) Appl. No.: 13/958,431

(22) Filed: Aug. 2, 2013

(65) Prior Publication Data
US 2014/0039575 A1 Feb. 6, 2014

Related U.S. Application Data

(60) Provisional application No. 61/679,374, filed on Aug. 3, 2012.

(51) Int. Cl.
*A61N 1/36* (2006.01)
*A61N 1/05* (2006.01)
*A61B 5/0476* (2006.01)

(52) U.S. Cl.
CPC ....... *A61N 1/36003* (2013.01); *A61N 1/36103* (2013.01); *A61B 5/0476* (2013.01); *A61N 1/0551* (2013.01)

(58) Field of Classification Search
CPC ............ A61N 1/36003; A61N 1/36103; A61N 1/0551; A61N 1/4076; A61N 1/4519
USPC .......................................................... 607/48
See application file for complete search history.

(56) References Cited

U.S. PATENT DOCUMENTS

| | | | |
|---|---|---|---|
| 6,895,280 B2 | 5/2005 | Meadows et al. | |
| 7,650,184 B2 | 1/2010 | Walter | |
| 8,019,439 B2 | 9/2011 | Kuzma et al. | |
| 2002/0087201 A1* | 7/2002 | Firlik | A61N 1/0531 607/45 |
| 2004/0186532 A1* | 9/2004 | Tadlock | A61N 1/0529 607/48 |
| 2006/0095088 A1* | 5/2006 | De Ridder | A61N 1/3605 607/48 |
| 2007/0150036 A1 | 6/2007 | Anderson | |

OTHER PUBLICATIONS

U.S. Appl. No. 61/569,214, Entitled: Method for Direct Modulation of the Spinothalamic Tract, Inventor: Kerry Bradley, et al., filed Dec. 9, 2011.

* cited by examiner

Primary Examiner — Michael Kahelin
Assistant Examiner — Minh Duc Pham
(74) Attorney, Agent, or Firm — Lowe Graham Jones PLLC; Bruce E. Black (57) ABSTRACT

A method for treating a patient suffering from loss of muscle control and/or function in a body region after a stroke includes epidurally applying electrical stimulation to a spinocerebellar tract of the patient (e.g., at or above the vertebral level of the spinal cord where the sensory and motor mapping for the body region are located), thereby increasing cortical excitability and facilitating the patient regaining muscle control and/or function in the body region. The method may include using cortical mapping to determine a cortical region having a residual motor response in or near the body region, implanting an electrode in a lateral epidural space, and applying the electrical stimulation in a manner that causes excitability in the cortical region having the residual motor response, wherein the stimulation is applied by the implanted electrode. The method may include exercising the body region while simultaneously applying the electrical stimulation.

14 Claims, 8 Drawing Sheets

SYSTEM AND METHOD FOR POST-STROKE NEURAL REHABILITATION

RELATED APPLICATION DATA

The present application claims the benefit under 35 U.S.C. §119 to U.S. provisional patent application Ser. No. 61/679,374, filed Aug. 3, 2012. The foregoing application is hereby incorporated by reference into the present application in its entirety.

FIELD OF THE INVENTION

The present invention relates to tissue stimulation systems, and more particularly, to spinal cord stimulation systems.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic neuropathic pain syndromes, and the application of spinal cord stimulation has expanded to include additional applications, such as angina pectoralis, peripheral vascular disease, and incontinence, among others. Spinal cord stimulation is also a promising option for patients suffering from motor disorders, such as Parkinson's Disease, Dystonia and essential tremor.

An implantable SCS system typically includes one or more electrode-carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via a lead extension. The neurostimulation system may further include a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Thus, programmed electrical pulses can be delivered from the neurostimulator to the stimulation lead(s) to stimulate or activate a volume of the spinal cord tissue. In particular, electrical stimulation energy conveyed to the electrodes creates an electrical field, which, when strong enough, depolarizes (or "stimulates") the neural fibers within the spinal cord beyond a threshold level, thereby inducing the firing of action potentials (APs) that propagate along the neural fibers to provide the desired efficacious therapy to the patient.

Many patients have disability from loss of motor function and control following stroke, depending upon the extent and location of the injury. After a stroke, the cortex can reorganize both spontaneously and with physical therapy such that the patient can regain motor function and control. That is, cortical tissue that survives the stroke can be re-mapped (e.g., spontaneously or through physical therapy) to provide motor control for body regions that were previously controlled by cortical tissue that did not survive the stroke.

Cerebellar stimulation has been shown to potentiate functional recovery over physical therapy alone, ostensibly by increasing cortical excitability to facilitate cortical tissue re-mapping, and improve the relearning process. However, cerebellar stimulation requires highly invasive, deep brain surgery, which can add morbidity to patients whose function is already compromised from stroke. Additionally, deep cerebellar stimulation is not likely easily reversible. If the stimulation system is needed only for a few months or years post-implant, removal of cerebellar electrodes may not be straightforward.

Thus, there remains a need for a minimally invasive, reversible system for increasing cortical excitability through cerebellar pathways in order to treat stroke patients.

SUMMARY OF THE INVENTION

In accordance with one aspect of the present inventions, a method for treating a patient suffering from loss of muscle control and/or function in a body region after a stroke is provided. The method includes epidurally applying electrical activation energy to a spinocerebellar tract of the patient, thereby increasing cortical excitability and facilitating the patient regaining muscle function in the body region. One method includes exercising the body region while simultaneously applying the electrical activation energy. The electrical activation energy may be applied to a region of the spinocerebellar tract of the patient at or above the vertebral level of the spinal cord where the sensory and motor mapping for the body region are located. The electrical activation energy may be applied to the spinocerebellar tract by at least one electrode implanted within the lateral epidural space of the patient.

In accordance with another aspect of the present inventions, a method for treating a patient suffering from loss of muscle control and/or function in a body region after a stroke is provided. The method includes using cortical mapping (e.g., transcranial magnetic stimulation) to determine a cortical region having a residual motor response in or near the body region; implanting at least one electrode in a lateral epidural space of the patient; and applying electrical stimulation to a spinocerebellar tract of the patient in a manner that causes excitability in the cortical region having the residual motor response, wherein the stimulation is applied by the at least one electrode. The method may further include measuring a cortical response to the applied electrical stimulation using EEG or ECoG. Still further, the method may include exercising the body region while simultaneously applying the electrical stimulation. The electrical stimulation may be applied to a region of the spinocerebellar tract of the patient at or above the vertebral level of the spinal cord where the sensory and motor mapping for the body region are located.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
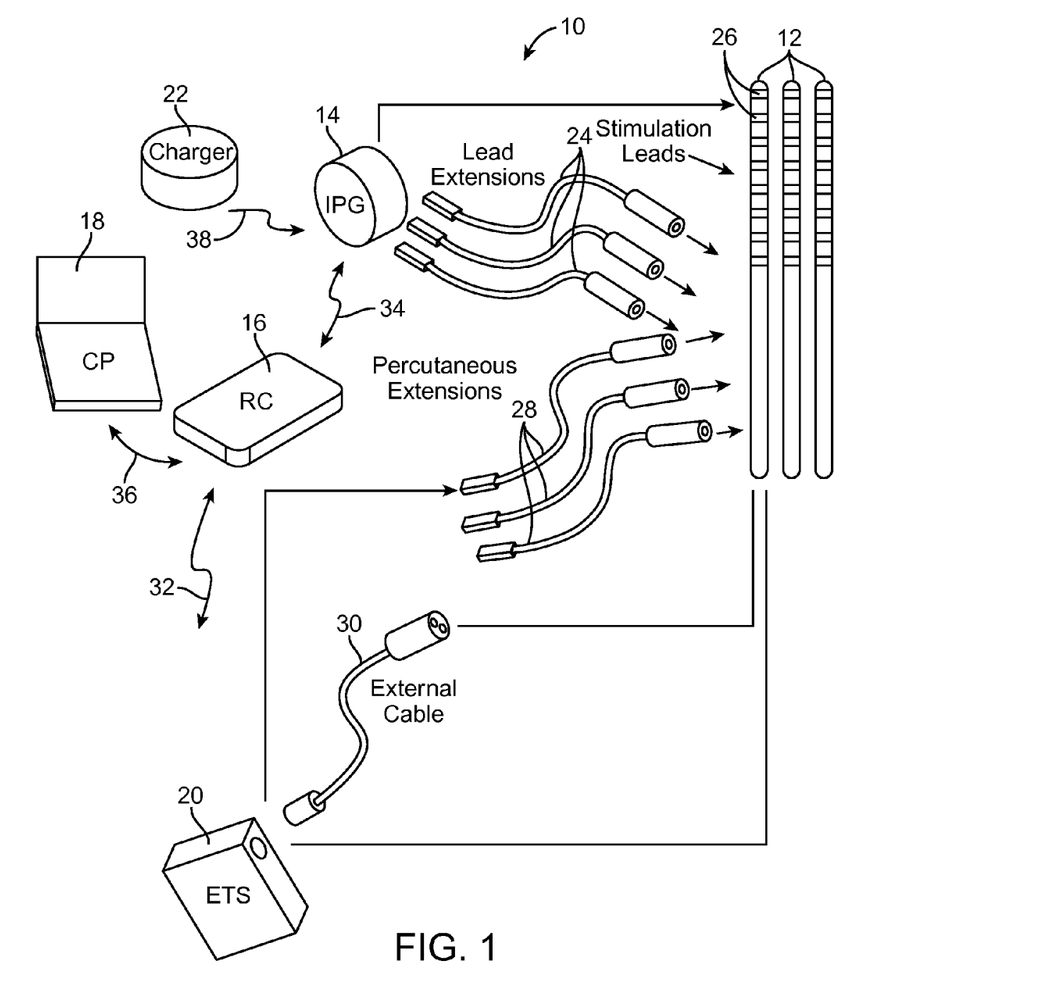
FIG. 1 is a plan view of a Spinal Cord Stimulation (SCS) system constructed in accordance with one embodiment of the present inventions.

Turning first to FIG. 1, an exemplary SCS system 10 generally comprises a plurality of stimulation leads 12 (in this case, three), an implantable pulse generator (IPG) 14 (or alternatively RF receiver-stimulator), an external remote control RC 16, a Clinician's Programmer (CP) 18, an External Trial Stimulator (ETS) 20, and an external charger 22.

The IPG 14 is physically connected via one or more lead extensions 24 to the stimulation leads 12, which carry a plurality of electrodes 26 arranged in an array. The stimulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via percutaneous lead extensions 28 and an external cable 30 to the neurostimulation leads 12. The ETS 20, which has similar pulse generation circuitry to the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
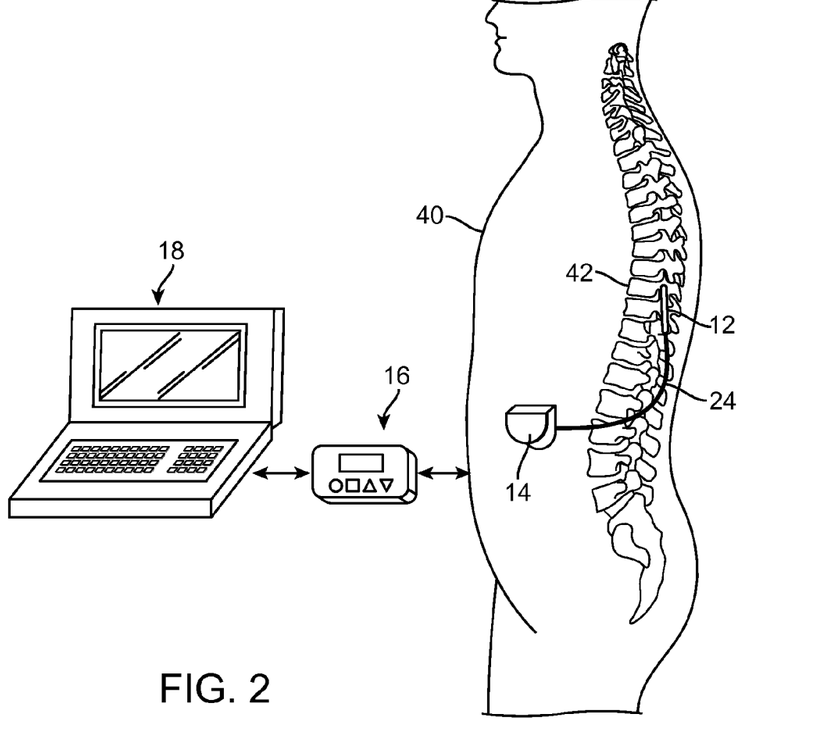
FIG. 2 is a plan view of the SCS system of FIG. 1 in use within a patient.

As shown in FIG. 2, the stimulation leads 12 are implanted within the spinal column 42 of a patient 40. The preferred placement of the electrode leads 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
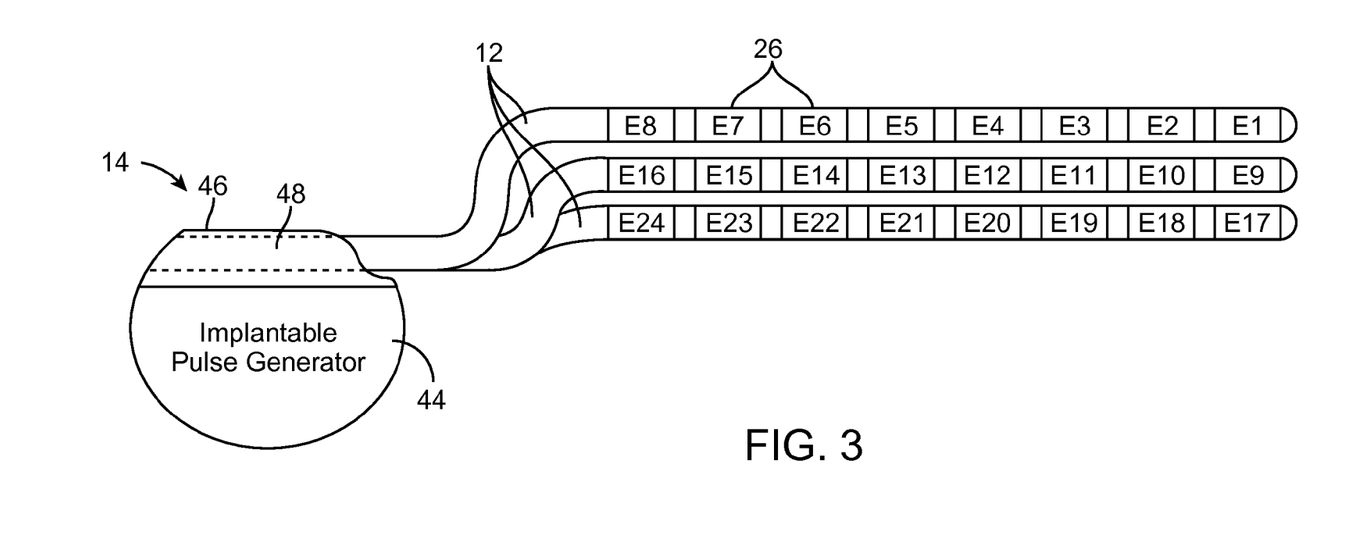
FIG. 3 is a plan view of an implantable pulse generator (IPG) and three percutaneous stimulation leads used in the SCS system of FIG. 1.

Referring now to FIG. 3, the external features of the stimulation leads 12 and the IPG 14 will be briefly described. Each of the stimulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are expressly incorporated herein by reference.

Figure 4:
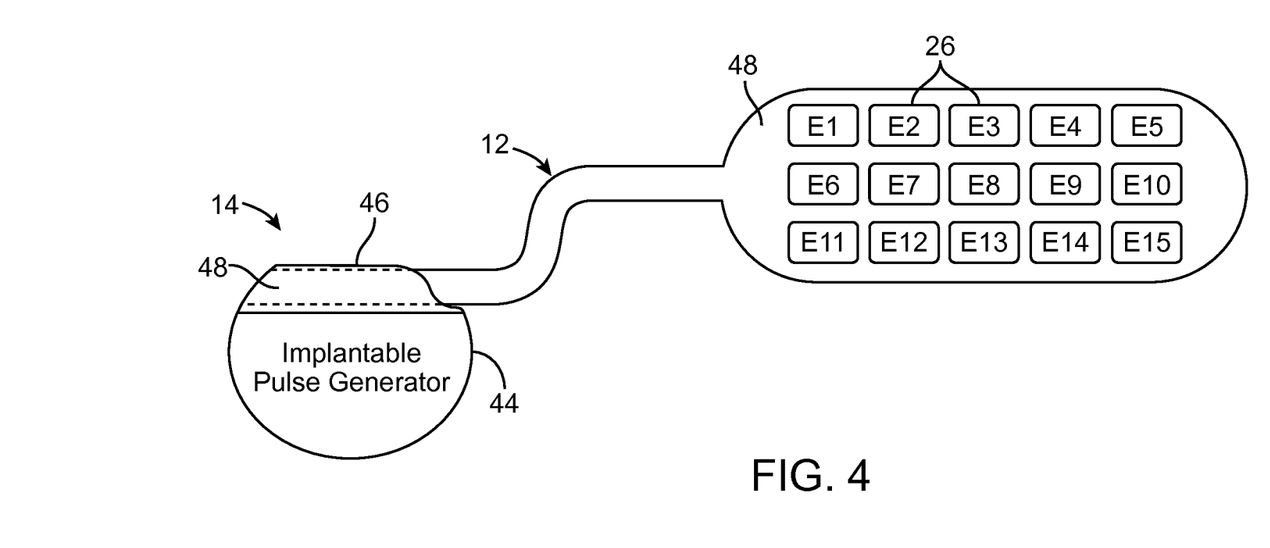
FIG. 4 is a plan view of an implantable pulse generator (IPG) and a surgical paddle lead used in the SCS system of FIG. 1.

Alternatively, as illustrated in FIG. 4, the stimulation lead 12 takes the form of a surgical paddle lead on which electrodes 26 are arranged in a two-dimensional array in three columns (respectively labeled E1-E5, E6-E10, and E11-E15) along the axis of the stimulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. Patent Application Publication No. 2007/

0150036, entitled "Stimulator Leads and Methods for Lead Fabrication," the disclosure of which is expressly incorporated herein by reference.

In each of the embodiments illustrated in FIGS. 3 and 4, the IPG 14 comprises an outer case 44 for housing the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The IPG 14 further comprises a connector 46 to which the proximal ends of the stimulation leads 12 mate in a manner that electrically couples the electrodes 26 to the internal electronics (described in further detail below) within the outer case 44. To this end, the connector 46 includes one or more ports 48 (three ports for three percutaneous leads or one port for the surgical paddle lead) for receiving the proximal end(s) of the stimulation lead(s) 12. In the case where the lead extensions 24 are used, the port(s) 48 may instead receive the proximal ends of such lead extensions 24.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 44. Simulation energy may be transmitted to the tissue in a monopolar or multipolar (e.g., bipolar, tripolar, etc.) fashion. Monopolar stimulation occurs when a selected one of the lead electrodes 26 is activated along with the case 44 of the IPG 14, so that stimulation energy is transmitted between the selected electrode 26 and the case 44. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 5:
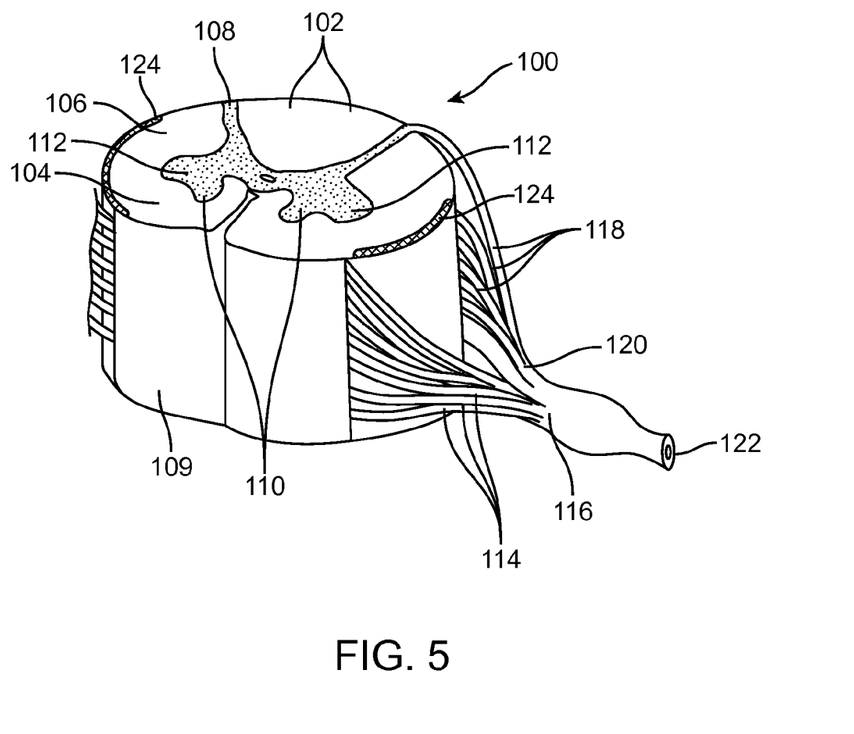
FIG. 5 is a peripheral view of the spinal cord and spinal nerves.
Figure 6:
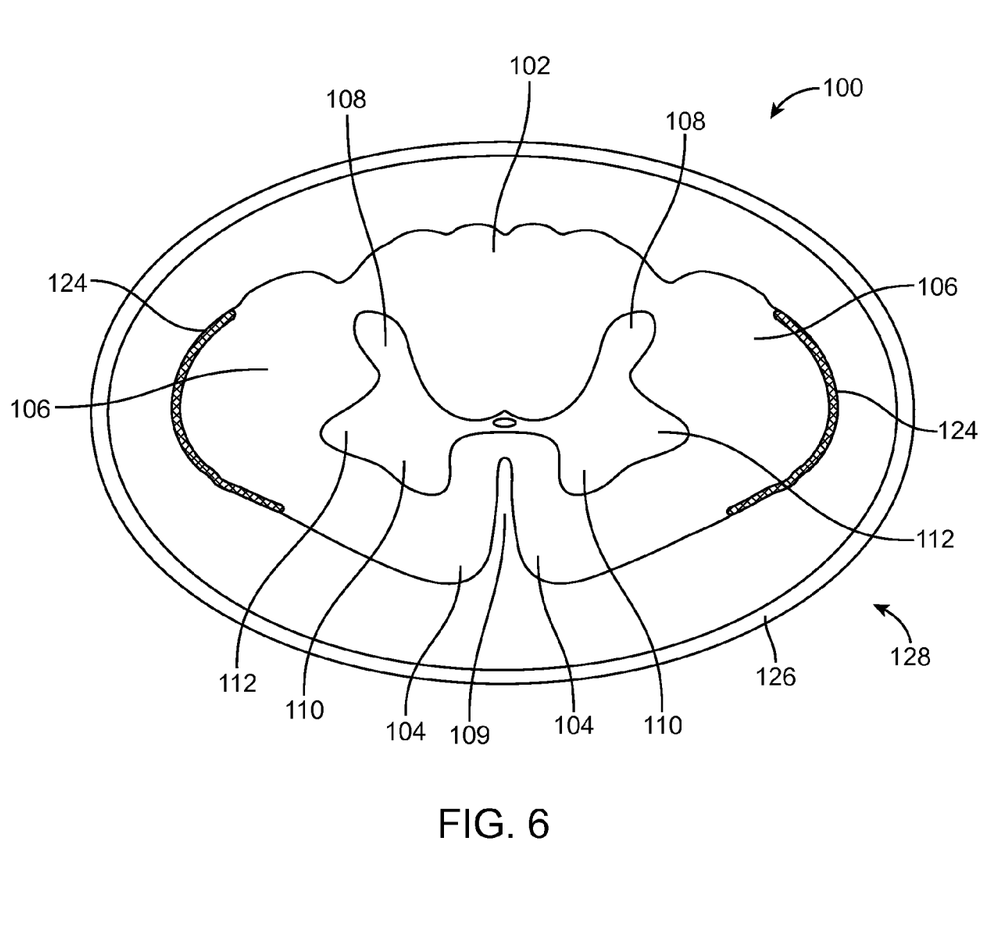
FIG. 6 is a cross-sectional view of the spinal cord.

Referring now to FIGS. 5 and 6, the portions of the spinal cord 100 that are relevant to the present inventions will be described. The spinal cord 100 is divided into three functional columns: the dorsal column 102, the ventral column 104, and the lateral column 106. Similarly, the butterfly-shaped gray matter of the spinal cord 100 is divided into the dorsal horn 108, the ventral horn 110, and the lateral horn 112. A ventral median fissure 109 divides the spinal cord 100 into two lateral halves.

A group of motor nerve rootlets (ventral root (VR) nerve fibers) 114 branch off of the ventral horn 110 and combine to form the ventral root 116. Similarly, a group of sensory nerve rootlets (dorsal root (DR) nerve fibers) 118 branch off of the dorsal horn 108 and combine to form the dorsal root 120. The dorsal root 120 and the ventral root 116 combine to form the spinal nerve 122, which innervates peripheral regions (e.g., arms, legs, etc.) of the patient's body. A number of spinal nerves branch off the spinal cord. In each patient, there are eight cervical spinal nerves designated C1-C8, twelve thoracic spinal nerves designated T1-T12, five lumbar spinal nerves designated L1-L5, and five sacral spinal nerves designated S1-S5.

The spinocerebellar tract 124 is a neural pathway in the lateral column 106 of the spinal cord 100. The spinocerebellar tract 124 includes bilaterally symmetrical portions lying on either side of the median fissure 109. This sensory pathway originates in the spinal cord and carries information to the cerebellum concerning limb and joint position. As a primary pathway for proprioceptive information, the spinocerebellar tract 124 offers an attractive target for increasing cortical excitability through cerebellar pathways.

The spinal cord 100 is enclosed by a dura mater 126, with an epidural space 128 surrounding the dura mater 126. In conventional SCS techniques, stimulation is applied to the dorsal column 102 of the spinal cord 100 to treat chronic neuropathic pain, and accordingly, stimulation leads are positioned in the dorsal region of the epidural space 128. As opposed to the conventional SCS techniques, the methods of the present invention stimulate the spinocerebellar tract 124 of the spinal cord 100 for post-stroke reconditioning and rehabilitation. To this end, the stimulation lead(s) 12 are preferably implanted within the lateral epidural space, such that the tip(s) of the stimulation lead(s) 12, and thus some of the electrodes 26, are located adjacent to the spinocerebellar tract 124 of the spinal cord 100.

Thus, electrical stimulation energy can be epidurally applied by the stimulation lead(s) to activate the spinocerebellar tract 124, thereby increasing cortical excitability to facilitate the patient regaining muscle control and/or function in a body region affected by stroke. The distal end(s) of the stimulation lead(s) 12 are preferably located at a position along the spinal cord 100 at or above the vertebral level of the spinal cord where the sensory and motor mapping are located for the body region experiencing loss of muscle control and/or function. Multiple leads may be positioned along the spinal cord 100 to treat multiple body regions suffering from loss of muscle control and/or function.

The electrical stimulation energy may be applied during exercise of the affected body region. Cortical tissue re-mapping may be facilitated by applying the electrical stimulation energy during post-stroke rehabilitation. For example, the electrical stimulation energy may be applied while the patient is undergoing physical therapy for the body region. Thus, the SCS system 10 may be pre-programmed (e.g., by programming the RC 16 and/or the IPG 14) to apply the electrical stimulation energy on a daily or weekly basis to coincide with regularly scheduled exercise, such as physical therapy or occupational therapy. In another embodiment, stimulation in accordance with pre-programmed stimulation parameters may be activated by the patient (e.g., through the RC 16) during exercise of the body region.

The stimulation may be delivered using multiple stimulation channels to selectively treat different body regions, or to be selectively applied during different exercises. For example, if the patient requires treatment in two different body regions that suffer loss of motor function, stimulation in accordance with two different stimulation parameter sets may be respectively applied through two different stimulation channels to respectively treat the two body regions. In another example, if a body region is subjected to two different exercises, it may be desirable for stimulation in accordance with two different stimulation parameter sets to be respectively applied during the two different exercises through the two different stimulation channels.

During application of the stimulation energy to the spinocerebellar tract 124, the activation threshold of neural structures (e.g., the VR nerve fibers 114 and/or DR nerve fibers 118) relative to the activation threshold of the spinocerebellar tract 124 is preferably increased, so that the neural structures are not inadvertently stimulated. Different techniques can be used to increase the activation thresholds of these neural structures relative to the activation threshold of the spinocerebellar tract 124. Such techniques are discussed in greater detail in U.S. Provisional Patent Application Ser. No. 61/569,214, which is expressly incorporated herein by reference.

In one embodiment, the stimulation leads(s) 12 are located within the cervical region of the spinal cord 100, wherein the sensitive VR nerve fibers 114 and DR nerve fibers 118 extend straight out from the spinal cord 100, thereby providing more spatial isolation between these nerve fibers and the spinocerebellar tract 124. As such, the distal tip(s) of the stimulation lead(s) 12 may be more easily located between the VR nerve fiber grouping 114 and/or DR nerve fiber grouping 118 rostral and caudal to the positioned stimulation leads. The electrodes 26 may be arranged relative to the VR nerve fiber grouping 114 and/or DR nerve fiber grouping 118 in any one of a variety of manners.

Figure 7:
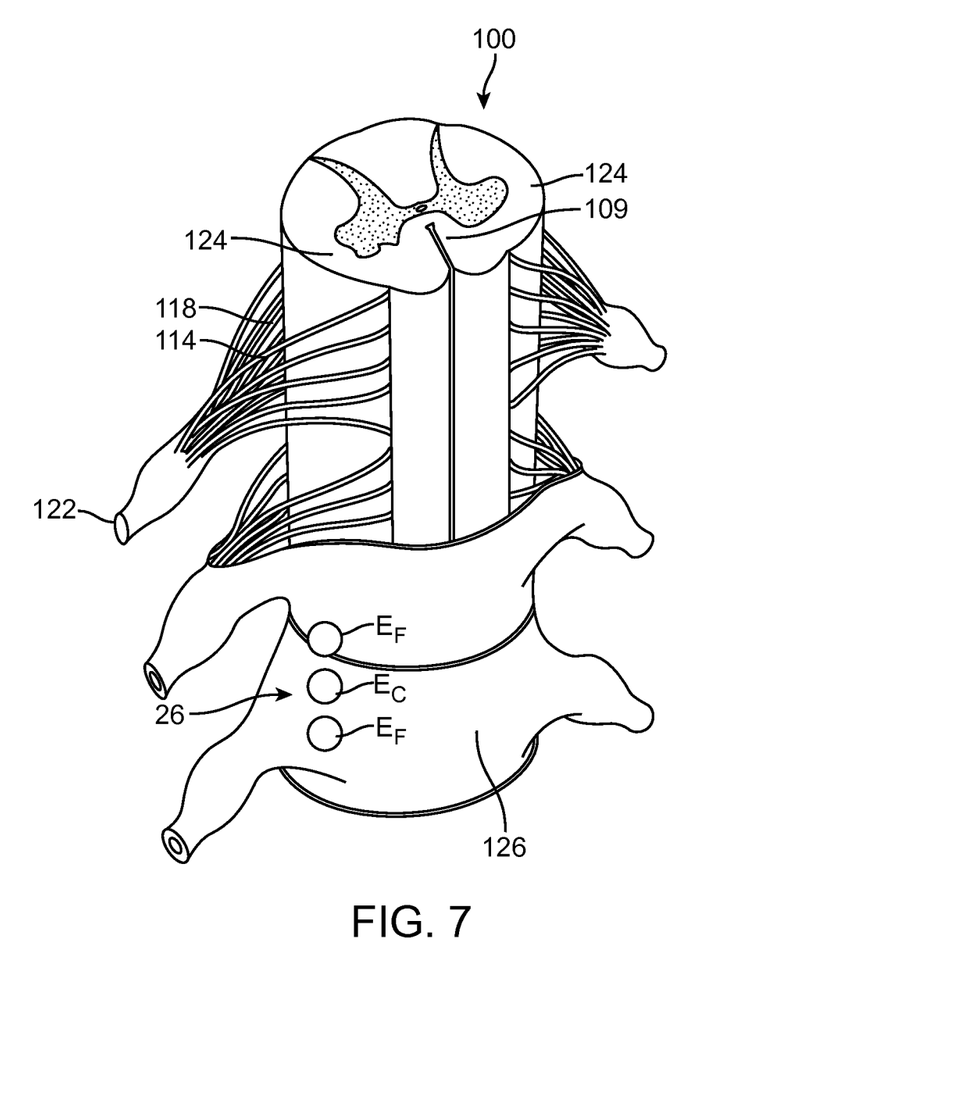
FIG. 7 is a perspective view showing one electrode arrangement relative to the spinal cord and spinal nerves in accordance with the present invention.

For example, in one embodiment illustrated in FIG. 7, a configuration of three electrodes 26 (labeled $E_C$ for the center electrode, and $E_F$ for the flanking electrodes) is aligned along the longitudinal axis of the spinal cord 100 (i.e., in the rostro-caudal direction) between a pair of VR nerve groupings 114, such that the flanking electrodes $E_F$ of the tripole configuration are respectively closest to the VR nerve fiber groupings 114. As seen more clearly in FIG. 7, the distal-most electrodes 26 are placed in the vicinity of, but not quite reaching, the ventral median fissure 109 at the center of the ventral side of the spinal cord 100. Alternatively, the electrode configuration may be obliquely aligned relative to the longitudinal axis of the spinal cord 100 between the ventral roots 116.

Figure 8:
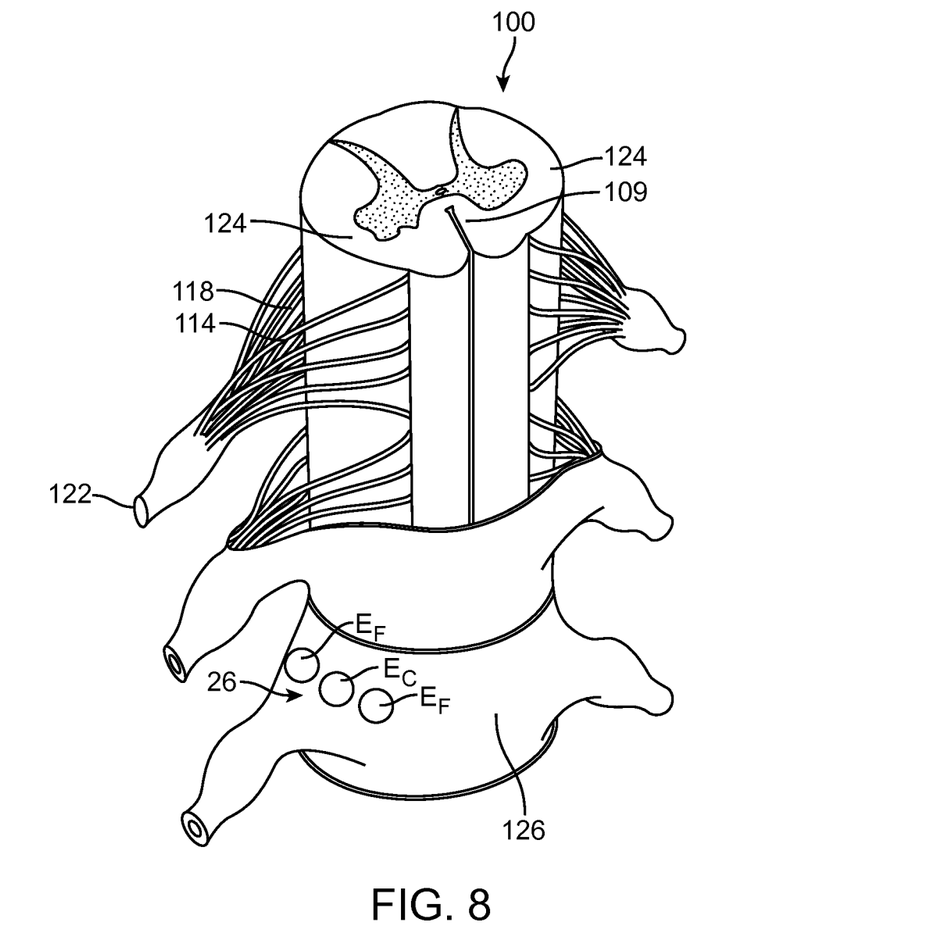
FIG. 8 is a perspective view showing another electrode arrangement relative to the spinal cord and spinal nerves in accordance with the present invention.

In another embodiment illustrated in FIG. 8, a configuration of three electrodes (labeled $E_C$ for the center electrode, and $E_F$ for the flanking electrodes) is aligned perpendicularly to the longitudinal axis of the spinal cord 100 (i.e., in the medial-lateral direction) between a VR nerve fiber grouping 114 and a DR nerve fiber grouping 118 at the same spinal level on one lateral side of the ventral medial fissure 109, such that the flanking electrodes $E_F$ are respectively closest to the VR nerve fiber grouping 114 and the DR nerve fiber grouping 118. Optionally, another configuration of three electrodes can be aligned perpendicularly to the longitudinal axis of the spinal cord 100 between a VR nerve fiber grouping 114 and a DR nerve fiber grouping 118 at the same spinal level on the other lateral side of the ventral medial fissure 109.

The electrode configurations illustrated in FIGS. 7 and 8 can be formed, e.g., using the distal-most electrodes 26 on three side-by-side percutaneous leads 12 (shown in FIG. 3) or the distal-most row of electrodes 26 on the surgical paddle lead 12 (shown in FIG. 4).

Cortical mapping may be used to determine a cortical region having residual motor response in or near the body region affected by the stroke. For example, transcranial magnetic stimulation may be used to determine a cortical region having residual motor response. The electrodes 26 may then be positioned and programmed so that the electrical stimulation is applied in a manner that causes excitability in the cortical region having the residual motor response. The cortical response to the electrical stimulation may be measured using electroencephalography (EEG) or electrocorticography (ECoG) to determine whether the electrical stimulation is affecting the cortical region having residual motor response. The SCS 10 may be programmed so that the EEG or ECoG indicates that the effects of the stimulation are maximized near the cortical regions exhibiting residual motor response.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for treating a patient suffering from at least one of loss of muscle control and loss of muscle function in a body region after a stroke, the method comprising:
  epidurally applying electrical activation energy to a spinocerebellar tract of the patient using one or more of a plurality of electrodes implanted within an epidural space of the patient adjacent a lateral column of a spinal cord of the patient and to one lateral side of a ventral medial fissure of the spinal cord of the patient, thereby increasing cortical excitability and facilitating the patient regaining at least one of muscle control and muscle function in the body region.

2. The method of claim 1, further comprising exercising the body region while simultaneously applying the electrical activation energy.

3. The method of claim 1, wherein the electrical activation energy is applied to a region of the spinocerebellar tract of the patient at or above the vertebral level of the spinal cord where the sensory and motor mapping for the body region are located.

4. The method of claim 1, wherein the plurality of electrodes comprises at least three electrodes implanted between a pair of ventral root nerve fiber groupings.

5. The method of claim 4, wherein the at least three electrodes are aligned along a longitudinal axis of the spinal cord.

6. The method of claim 5, wherein each of the at least three electrodes is disposed on a different lead.

7. The method of claim 1, wherein the plurality of electrodes comprises at least three electrodes implanted between a ventral root nerve grouping and a dorsal root nerve fiber grouping at a same spinal level.

8. The method of claim 7, wherein the at least three electrodes are aligned perpendicularly to a longitudinal axis of the spinal cord.

9. The method of claim 8, wherein the plurality of electrodes comprises at least three additional electrodes implanted between a ventral root nerve grouping and a dorsal root nerve fiber grouping on a second lateral side of the ventral medial fissure of the spinal cord of the patient, wherein the second lateral side is opposite the first lateral side relative to the ventral medial fissure.

10. The method of claim 1, further comprising:
determining a cortical region having a residual motor response in or near the body region using cortical mapping;
wherein epidurally applying electrical activation energy comprises applying electrical stimulation to the spinocerebellar tract of the patient to cause excitability in the cortical region having the residual motor response.

11. The method of claim 10, further comprising measuring a cortical response to the applied electrical stimulation using EEG or ECoG.

12. The method of claim 10, wherein determining a cortical region comprises determining a cortical region having a residual motor response in or near the body region using transcranial magnetic stimulation.

13. The method of claim 1, further comprising implanting the plurality of electrodes within an epidural space of the patient adjacent the lateral column of the spinal cord of the patient and to the first lateral side of the ventral medial fissure of the spinal cord of the patient.

14. The method of claim 1, wherein the plurality of electrodes are implanted in a cervical region of the spinal cord.

* * * * *